(12) United States Patent
Williams

(10) Patent No.: US 6,190,395 B1
(45) Date of Patent: Feb. 20, 2001

(54) IMAGE GUIDED UNIVERSAL INSTRUMENT ADAPTER AND METHOD FOR USE WITH COMPUTER-ASSISTED IMAGE GUIDED SURGERY

(75) Inventor: Thomas R. Williams, Boulder, CO (US)

(73) Assignee: Surgical Navigation Technologies, Inc., Broomfield, CO (US)

( * ) Notice: Under 35 U.S.C. 154(b), the term of this patent shall be extended for 0 days.

(21) Appl. No.: 09/296,251

(22) Filed: Apr. 22, 1999

(51) Int. Cl.[7] ........................................... A61B 19/00
(52) U.S. Cl. ................................. 606/130; 600/424
(58) Field of Search ........................... 606/130; 600/424, 600/425, 426

(56) References Cited

U.S. PATENT DOCUMENTS

| | | | |
|---|---|---|---|
| 5,257,998 | * 11/1993 | Ota et al. | 606/130 |
| 5,762,458 | * 6/1998 | Wang et al. | 414/1 |
| 5,768,751 | * 6/1998 | Oetiker | 24/40 |
| 6,006,127 | * 12/1999 | Van Der Brug et al. | 600/427 |
| 6,021,343 | * 2/2000 | Foley et al. | 600/429 |

* cited by examiner

*Primary Examiner*—Paul J. Hirsch
*Assistant Examiner*—Michael B. Priddy
(74) *Attorney, Agent, or Firm*—Finnegan, Henderson, Farabow, Garrett & Dunner, LLP

(57) ABSTRACT

An apparatus is disclosed for use with a surgical navigation system. The apparatus comprises a universal instrument attachment device. The universal instrument attachment device preferably includes a tracking body onto which a position tracking array is fixedly mountable, and an instrument attachment body removably and adjustably mounted to the tracking body. The instrument attachment body further includes a flexible clamping band having a circumference for adaptably conforming around a variety of instruments having different circumferential shapes and clamping the instrument to the instrument attachment body itself.

23 Claims, 3 Drawing Sheets

IMAGE GUIDED UNIVERSAL INSTRUMENT ADAPTER AND METHOD FOR USE WITH COMPUTER-ASSISTED IMAGE GUIDED SURGERY

BACKGROUND OF THE INVENTION

1. Field of the Invention

The present invention relates to a system that assists in the performance of a surgical procedure by generating images to illustrate the relative position of various body parts and instruments during the surgical procedure, and, more particularly, to an image guided system that employs a position tracking device that is adjustably mounted to an instrument.

2. Description of the Related Art

In recent years, a variety of different types of surgical navigation systems have been introduced in order to improve the performance of surgical procedures. For instance, U.S. Pat. Nos. 5,383,454; 5,851,183; 5,871,445; and 5,891,034 to Bucholz; PCT Application No. PCT/US94/04530 (Publication No. WO 94/24933) to Bucholz; and PCT Application No. PCT/US95/12894 (Publication No. WO 95/11624) to Bucholz et al., the entire disclosures of each of which is incorporated herein by reference, disclose surgical navigation systems that illustrate the position of medical instruments during surgical procedures.

A typical navigation system employs a scanner to generate images for indicating the position of a medical instrument relative to a predetermined body part, for example. Moreover, such surgical navigation systems typically include position tracking devices, such as for example, a position indicating LED and/or reflector array arranged about a body part as well as position indicating LEDs and/or reflectors mounted on a medical instrument, which are part of a position sensing device further including a digitizer camera to track the positions of the selected body parts and medical instruments, and a display for illustrating the relative positions of the body party and the medical instrument during the medical procedure.

Although these types of systems can be effective, additional improvements are desirable to facilitate the mating of medical instruments to position tracking devices. For example, accurate illustration of the precise position of a medical instrument is of paramount importance in virtually any image guided medical procedure. This is true because a primary purpose of utilizing a navigation system is to allow an operator to perceive accurately the precise location of a body part relative to the location of the medical instrument being implemented. If a medical instrument is not adequately mounted to the position tracking device, then the navigation system may lose information about the precise location of the medical instrument relative to the position tracking device. Consequently, an inaccurate illustration of the location of the medical instrument relative to a body part may result.

With this in mind, typical surgical navigation systems employing known mounting devices can suffer from several important drawbacks. In conventional navigation systems, for example, rigid clamping brackets, e.g., in the form of a "C" clamp, and associated clamping screws may be used to attach medical instruments to respective position tracking devices. As such, the amount of frictional clamping force available in such conventional clamping bracket designs may be inherently limited. This is so because the contact area between conventional brackets and medical instruments is restricted to a point or along a line. Thus, conventional bracket mechanisms may increase the likelihood that an inaccurate illustration of the position of a medical instrument will occur, as discussed above, because the stability of conventional position tracking mounting devices may be compromised.

As another example, known position tracking mounting devices are not capable of satisfactorily accommodating a wide variety of medical instrument shapes and sizes. Indeed, known clamping devices may need to be replaced each time a medical instrument having a different shape and/or size is desired. In particular, known mounting designs contemplate the use of custom made position tracking mounting mechanisms for medical instruments that are of a different size or shape. Moreover, when using a plurality of different instruments in a single surgical procedure, known position tracking mounting arrangements can fail to facilitate efficient replacement of a variety of medical instruments having different sizes and shapes. As a result, known position tracking mounting devices require unnecessary time, expense and inconvenience.

Additionally, conventional surgical navigation systems employ position tracking mounting devices that can fail to adequately address the hazards of introducing new medical instruments into a surgical field prior to and/or during a surgical procedure. Namely, if a new medical instrument is introduced into a surgical procedure without re-calibrating the position of the newly introduced instrument relative to a known reference point, then inaccurate illustration of the position of the medical instrument on the display can result as discussed above. Accordingly, a simple and reliable way to require an operator to properly re-calibrate and/or re-register the position of a newly introduced medical instrument is desirable.

As a further example, typical surgical navigation systems employ known position tracking devices that are not always adjustably mounted in a stable manner to a medical instrument in a variety of geometric configurations. Adjustably mounting a medical instrument to a position tracking device is advantageous for a number of important reasons. For instance, a clear line of sight between the digitizer camera and the emitters and/or reflectors of the position tracking should be maintained throughout the medical procedure, itself. If this line of sight is interrupted, then inaccurate illustration of the position of the medical instrument can result, as discussed above. In practice, it is advantageous for a surgeon to be able to position the medical instrument in a particular orientation. In order to position the medical instrument as such, the emitters and/or reflectors of the conventional position tracking device may be forced to point away from the digitizer camera. However, if the position tracking device is adjustably mounted relative to the medical instrument in a stable manner, then the emitters and/or reflectors can be controlled to be continuously directed toward the digitizer camera while the medical instrument is placed in a particular orientation.

In light of the foregoing, there are a need for an improved image guided universal attachment device in surgical navigation systems.

SUMMARY OF THE INVENTION

The advantages and purpose of the invention will be set forth in part in the description which follows, and in part will be obvious from the description, or may be learned by practice of the invention. Moreover, the advantages and purposes of the invention will be realized and attained by means of the elements and combinations particularly pointed out in the appended claims.

To attain the advantages and in accordance with the purpose of the invention, as embodied and broadly described herein, the present invention is directed to an image guided system for use in performing operative procedures with an instrument comprising
a computer controlled navigation arrangement having a controller in communication with a sensor array for interacting with a position tracking array and tracking positions of the instrument in three dimensional space relative to a known reference point, a tracking head supporting the position tracking array, an instrument mounting assembly attachable to the instrument, and a quick release coupling for connecting the tracking head to the instrument mounting assembly.

In another aspect, the advantages and purpose of the present invention are attained by an instrument attachment device for use with a computer controlled surgical navigation system employing a controller in communication with a sensor array for interacting with an instrument mounted position tracking array and tracking positions of an instrument in three dimensional space relative to a known reference point. The instrument attachment device comprises a tracking head carrying the position tracking array, and an instrument mounting assembly having a compliant clamping band attachable to the instrument, and a head connector enabling adjustment of the angle between the tracking head and the instrument.

In yet another aspect, the advantages and purpose of the present invention are realized by a method of computer controlled surgical instrument navigation in which a controller communicates with a sensor array for interacting with an instrument mounted position tracking array on a tracking head and tracks positions of an instrument in three dimensional space relative to a known reference point. The method comprises the steps of fixedly mounting an instrument mounting assembly to each of a plurality of surgical instruments to be used in a surgical procedure, providing for a quick release coupling of the tracking head to the mounting assembly on each of the plurality of surgical instruments, and signalling the controller for each connection and disconnection of the tracking head to each surgical instrument.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

DESCRIPTION OF THE PREFERRED EMBODIMENTS

Reference will now be made in detail to the preferred embodiments of the invention, examples of which are illustrated in the accompanying drawings. Wherever possible, the same reference numbers will be used throughout the drawings to refer to the same or like parts.

The present invention provides an image guided system for use in performing surgical or other medical procedures with an instrument. The image guided system includes computer controlled navigation arrangement having a controller in communication with a sensor array for interacting with a position tracking head and for tracking positions of the instrument in three dimensional space relative to a known reference point.

Figure 1:
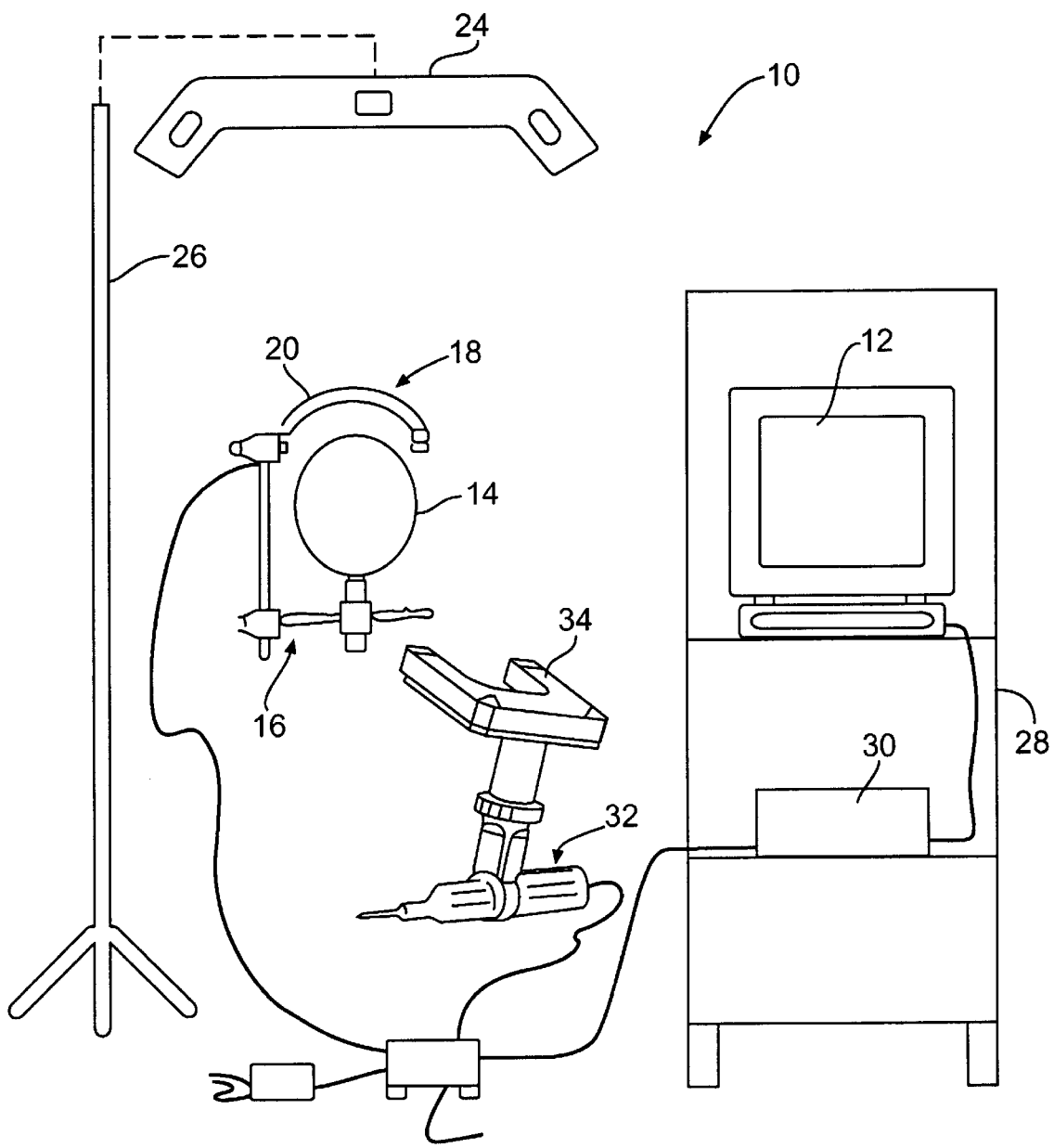
FIG. 1 is a schematic diagram of one preferred embodiment of a surgical navigation system with an image guided universal instrument adapter.

In the illustrated embodiment, as shown in FIG. 1, a computer assisted image guided surgery system, designated generally by the reference numeral 10, generates an image for display on a monitor 12 representing the position of one or more body elements, such as a cranium represented by circle 14 fixedly held in a well-known clamping device such as a Mayfield clamp assembly 16. A reference arc 18, bearing tracking means such as LED emitters or reflectors 20, for example, is mounted to the Mayfield clamp 16. The image is generated from an image data set, usually pre-operatively by a CAT scanner for example, which image has reference points for at least one body element, such as cranium 14. The reference points of the particular body element have a fixed spatial relation to the particular body element.

The illustrated system 10 further includes a Position Sensing Unit (PSU), such as a digitizer camera 24 on a support 26 for identifying, during a surgical procedure, for example, the relative position of each of the reference points to be displayed by tracking the position of emitters/reflectors 20 on arc 18 as shown in FIG. 1. The system 10 also includes a processor 28, such as PC or other suitable workstation processor, with an associated controller 30 for modifying the image data set according to the identified relative position of each of the reference points during the procedure, as identified by digitizer camera 24. The processor 28 can then, for example, generate a displaced image data set representing the position of the body elements during the procedure for display on monitor 12. An instrument 32, which may be any of a wide assortment of medical instruments, is fitted with a tracking head 34 in a manner to be further described in detail below. The instrument 32 is used during the medical or surgical procedure and thus positioned relative to a body part, such as cranium 14, to be tracked by the digital camera or suitable sensor array 24 and may be a drill, probe, catheter, biopsy guide, or any other suitable medical instrument having any particular shape and/or size capable of carrying out any desired procedure. A further description of the operation of the surgical navigation system 10 is found in the above-cited PCT/US95/12894, the entire disclosure of which is incorporated herein by reference.

In accordance with the present invention, the described image guided system includes an instrument tracking head and instrument mounting assembly by which the tracking head is fixed to the medical instrument of the system. The mounting assembly provides for a quick release and/or replacement of the tracking head and the instrument as well as adjustment of relative positional orientation between the tracking head and the instrument. Additionally, the instrument attachment body preferably comprises a flexible clamping band arrangement assuring a firm connection of the tracking head and the instrument and which is adaptable to a wide variety of instrument sizes and shapes.

Figure 2:
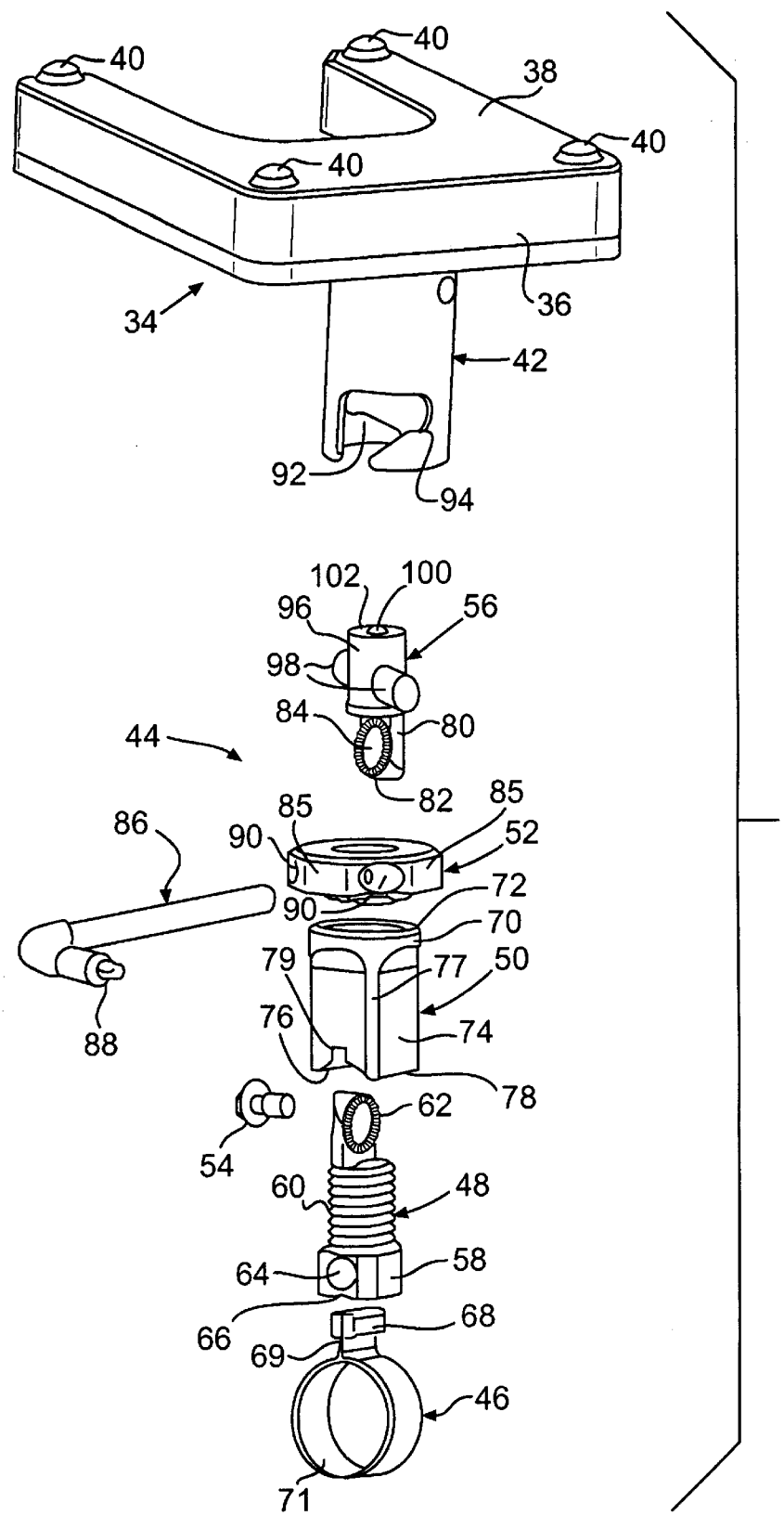
FIG. 2 is a exploded perspective view of an instrument attachment device according to a first embodiment of the present invention.

In a preferred embodiment illustrated in FIG. 2, tracking head 34 includes a generally U-shaped body 36 having a top surface 38 on which an array of light emitting/reflecting elements 40, is presented. Where the elements 40 are light emitting, light emitting diodes are preferably used. Alternatively, various forms of light reflective elements may be used. Tracking head 34 is supported on a mounting column 42 depending from the bottom thereof for connection to a instrument mounting assembly generally designated by the reference numeral 44.

Instrument mounting assembly 44 includes as separate components, a clamping band 46, a mounting post 48, a saddle collar 50, a clamp nut 52, a bolt 54 and a head connector 56.

Mounting post 48 includes a base portion 58 at one end, a central threaded portion 60, and a radially serrated coupling portion 62 at the other end. The periphery of base portion 58 is preferably of a chamfered rectangular or square configuration but may be of other non-circular peripheral configurations. A bore 64 extends diametrically through base portion 58 and opens through the bottom thereof via a slot 66 parallel to bore 64.

Clamping band 46 is preferably formed from a strip of low carbon stainless steel foil of a thickness in the range of 5 mils to 50 mils, preferably in the range of 10 mils to 30 mils, and more preferably 20 mils, and of a width approximating 0.25 inch to provide a compliant and yet suitably strong clamping band. As shown in FIG. 2, opposite ends of clamping band 46 are folded on themselves and brought together against each other to form an enlarged anchoring bead 68 spaced by a neck portion 69 from a closed loop portion 71 of clamping band 46. Enlarged anchoring bead 68 is receivable in the bore 64 of mounting post base portion 58 with neck portion 69 in slot 66, bead 68 being incapable of passing though slot 66. The construction of clamping band 46 enables customizing of the length of the band to fit any instrument diameter simply by cutting the appropriate length of strip and folding the ends to provide the enlarged anchoring bead 68. It is preferred, however, that the clamping bands are preformed and made available in sets with bands within each set having varying length to accommodate anticipated variations in instrument diameter. For example, a set may include four clamping band sizes where a first clamping band size fits a range of instruments 32, such as for example, between 0.125 inches and 0.25 inches in circumference; a second clamping band size accommodates a second range of instruments 32 between 0.25 and 0.375 inches in circumference; a third clamping band size fits a range of instruments 32 between 0.375 and 0.5 inches in diameter; and a fourth clamping band size is customly sized to be within 0.25 inches of the circumference of a given instrument 32.

Figure 3:
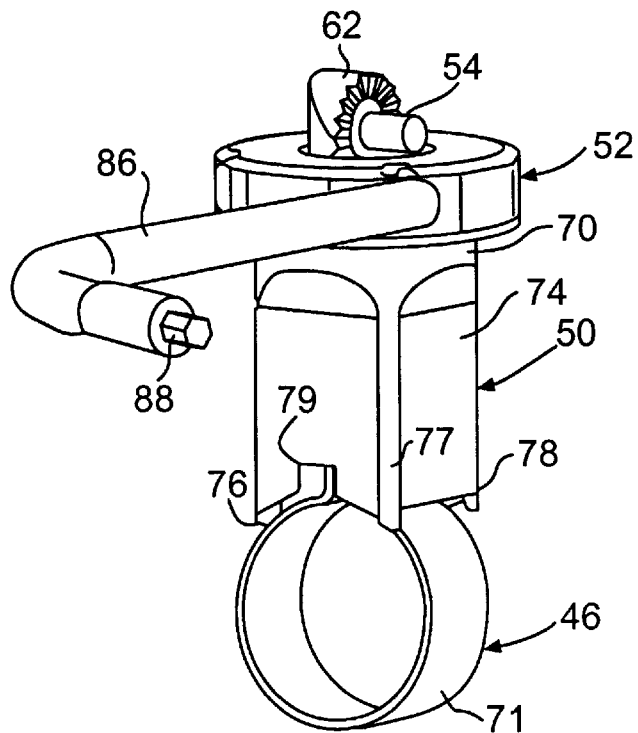
FIG. 3 is a assembled perspective view of an instrument attachment body according to the present invention.

As shown in FIG. 2, the upper end 70 of saddle collar 50 is circular to provide an annular nut bearing top surface 72. A major lower portion 74 of saddle collar 50 is of chamfered rectangular of square configuration so that the inside of lower portion 74 complements the shape of base portion 58 on mounting post 48 to prevent relative rotation of mounting post 48 and saddle collar 50 and guide relative axial movement of mounting post 48 within saddle collar 50. The bottom end of saddle collar 50 is defined by opposite arcuate or saddle-shaped edges 76 in one orthogonal direction, by the bottoms of chamfered corners 77, and by linear band clamp guiding edges 78 in the other orthogonal direction. As shown in FIGS. 2 and 3, linear guiding edges 78 are preferably elevated above the bottoms of chamfered corners 77 to allow free sliding movement of clamping band 46 without binding between linear guiding edges 78 and the peripheral surface of instrument 32. The radius of the arcuate edges 76 is selected to approximate one half of the anticipated largest diameter of instrument 32 on which the mounting assembly 44 will used to assure that linear guiding edges 78 will be spaced from the peripheral surface of instrument 38. Notches 79 are provided in the center of each arcuate edge 76 to provide stable engagement of saddle collar with the smallest diameter instrument 38 to be used, and to provide for proper engagement of rectangular flat instruments, such as forceps.

An assembled state of clamping band 46, mounting post 48, saddle collar 50, and clamp nut 52 is shown in FIG. 3. The assembly is accomplished by inserting enlarged anchoring bead 68 into bore 64 of mounting post base 58 with neck 69 in slot 66. Saddle collar 50 is then placed over mounting post 48 and located axially thereon so that at least a leading thread at the top of threaded portion 60 is exposed above top surface 72 of saddle collar 50. Clamp nut 52 is then engaged with the leading threads of threaded portion 60 to secure the assembly in an initial loose condition with base 58 within lower portion 74 of saddle collar 50 and loop portion 71 of clamping band 46 hanging loosely from base portion 58 of mounting post 48. In practice, bolt 54 is preferably captured in threaded hole 84 to prevent complete separation of it, head connector 56, and coupling portion 62.

In the initial loosely assembled condition of band clamp 46, mounting post 48, saddle collar 50 and clamp nut 52, radially serrated coupling portion 62 on mounting post 48 projects above clamp nut 52 to be fully accessible. Head connector 56, which includes a coupling portion 80 having a radially serrated face 82 that complements radial serrated coupling portion 62, and a threaded hole 84 to receive the threaded shank of bolt 54, may be mounted by bolt 54 to coupling portion 62.

The loosely interconnected mounting assembly 44 may be connected to instrument 32 by advancing loop portion 71 of clamping band 46 over one end of and axially relative to instrument 32 to a position of attachment to the latter. Clamp nut 52 is then tightened to draw loop portion 71 of clamping band 46 snugly about instrument 32 by applying tension to clamping band 46 as a result threaded movement of mounting post 48 against a compressive reaction in saddle collar 50. Alternatively, if the shape of instrument 32 does not permit the loose loop portion 71 of clamping band 46 to fit over an end of instrument 32 and/or be advanced axially to the position of clamping band attachment, clamping band 46 may be opened by separating the opposite ends thereof and placed directly about instrument 32 at the position of attachment. The opposite ends of clamping band 46 are then closed on each other to provide the anchoring bead 68. Mounting post 48 is manipulated to locate anchoring bead 68 of the preplaced clamping band 46 in bore 64 and the assembly of saddle collar 50 and clamp nut 52 is effected as described above.

Preferably, and as shown in FIG. 2, the periphery of clamp nut 52 is formed with opposed spanner flats 85 to enable application of tightening or loosening torque by hand or by using a conventional spanner wrench. Bolt 54 is preferably provided with a socket head to enable threaded placement, removal or adjustment using a conventional alien wrench. To enable application of tightening or loosening torque to both clamp nut 52 and bolt 54 by the same tool, a modified alien wrench 86 is supplied. As shown in FIG. 2, wrench 86 is an L-shaped cylindrical rod having an alien wrench head 88 on one end for application to bolt 54. Clamp nut 52 is provided with at least one, preferably four, chord oriented holes 90 opening through equally spaced spanner flats 85. Holes 90 are sized to receive the end of wrench 86 in a manner so that torque may be applied to clamping nut 52 in either direction of rotation by using wrench 86.

In the illustrated embodiment, tracking head 34 is secured to instrument mounting assembly 44 for quick connect/disconnect coupling of mounting column 42 on tracking head 34 and head connector 56 of the described instrument mounting assembly 44. In particular, the bottom end of mounting column 42, as shown in FIG. 2, is provided with an upwardly extending cylindrical socket 92 having diametrically oriented bayonet slots 94 opening through the periphery of mounting column 42. Head connector 56, in turn is provided with a cylindrical plug portion 96 having diametrically extending lugs 98 and a convex, spring-biased, ball detent projection 100 located centrally on a radial end face 102 of the plug portion 96.

To install track head 34 on a particular instrument 32 to which mounting assembly 44 has been fixed in the manner described, during a surgical procedure, an operator preferably aligns plug portion 96 with cylindrical socket 92, or vice versa, inserts plug portion 96 into socket 92, and rotates mounting column 42 relative to plug portion 96 of head connector 56 so that lugs 98 engage in bayonet slots 94. Engagement of ball detent projection 100 with the base end of cylindrical socket 92 will impart a biased retention of lugs 98 in bayonet slots 94. Removal of track head 34 involves only a reversal of the relative rotation of mounting column 42 and head connector 56 in a pull and twist mode of manipulation. Thus, the quick disconnect mounting arrangement allows an operator to remove an instrument 32 attached to tracking head 34 and replace it with another in a convenient and rapid fashion.

Also the angular position of tracking head 34 and instrument 32 may be adjusted to position instrument 32 in a desirable orientation without interrupting a line of sight between the array of light emitting/reflecting elements 40 and digitizer camera 24. Such adjustment is accomplished in the illustrated embodiment by loosening bolt 54 to release engagement of the radial serrations on the respective coupling portions 62 and 80, rotating the coupling portions about the axis of bolt 54 and tightening bolt 54 using wrench 86.

Where tracking head 34 includes electric circuitry associated with controller 30, mounting column may include a sensing device capable of providing a signal in response to the attachment or detachment of mounting column 42 to instrument mounting assembly 44 so that a signal is sent to the controller 30 indicating that a calibration and/or registration procedure needs to be performed. Such a calibration and/or registration procedure is effected to assure that information transmitted to controller 30 from tracking head 34 via digitizer camera 24 includes a precise relation of the working portion of instrument 32 relative to tracking head 34.

Figure 4:
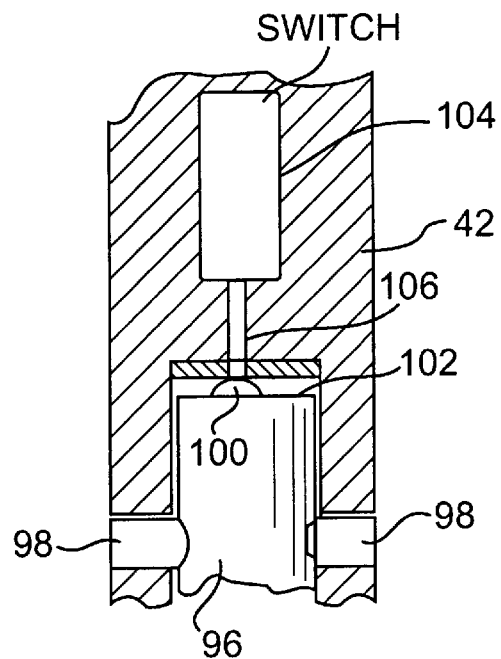
FIG. 4 is a schematic cross-section depicting a signal switch arrangement of the invention.

In the illustrated embodiment, and as shown very schematically in FIG. 4, a switch 104 having an actuator 106 is positioned in mounting column 42 so that actuator 106 is presented at the inner end of cylindrical socket 92. As the cylindrical plug portion 96 of head connector 56 is introduced into cylindrical socket 92, ball detent projection 100 will engage actuator 106 and change the state of switch 104. Correspondingly, removal of tracking head 34 from instrument mounting assembly 44, causing withdrawal of plug portion 96, will return switch 104 to its initial state.

In use, the mounting assembly of the invention, may be mounted to each of a plurality of surgical instruments to be used in a surgical procedure, for example. As each such instrument is needed during the procedure, the quick release coupling of the tracking head to the mounting assembly on each of the plurality of surgical instruments minimizes the time required for each instrument change. Also controller 30 will be informed of each change by the state of switch 104 of tracking head 34.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An image guided system for use in performing operative procedures with an instrument comprising:

a computer controlled navigation arrangement having a controller in communication with a sensor array for interacting with a position tracking array and tracking positions of the instrument in three dimensional space relative to a known reference point;

a tracking head supporting the position tracking array;

an instrument mounting assembly attachable to the instrument; and a quick release coupling for connecting the tracking head to the instrument mounting assembly.

2. The image guided system of claim 1, wherein the instrument mounting assembly includes a clamping band for engaging a periphery of the instrument.

3. The image guided system of claim 2, wherein the clamping band is a strip of low carbon stainless steel foil.

4. The image guided system of claim 3, wherein the strip of low carbon stainless steel foil has a thickness in the range from about 5 to 50 mils.

5. The image guided system of claim 3, wherein the strip of low carbon stainless steel foil has a thickness in the range from about 10 to 30 mils.

6. The image guided system of claim 3, wherein the strip of low carbon stainless steel foil has a thickness of about 20 mils.

7. The image guided system of any one of claims 3–6, wherein the strip of low carbon stainless steel foil has a width of about ¼ inch.

8. The image guided system of claim 2, wherein the instrument mounting assembly comprises:

a threaded mounting post having one end engageable with the clamping band;

a saddle collar on the mounting post; and a clamp nut for moving the mounting post to tension the clamping band against reactive compression in the saddle collar.

9. The image guided system of claim 8, wherein the mounting post has a base portion on one end for connection to the clamping band.

10. The image guided system of claim 9, wherein the base portion of the mounting post has a transverse slotted bore for receiving an anchoring bead on the clamping band.

11. The image guided system of claim 10, wherein the anchoring bead is formed by folded end portions of the clamping band closed against each other.

12. The image guided system of claim 1, wherein the instrument mounting assembly includes a mounting post having a base portion at one end for connection to the instrument and a head connector mounted an end of the mounting post opposite the base portion.

13. The image guided system of claim 12, wherein the head connector is mounted for angular adjustment relative to the mounting post.

14. The image guided system of claim 13, wherein the head connector and the end of the mounting post opposite the base portion have complementing radially serrated face portions secured to each other by a threaded bolt.

15. The image guided system of claim 8, wherein the clamp nut further comprises at least one receiving hole for engagement by a tool for rotating the clamp nut on the mounting post.

16. The image guided system of claim 8, wherein an end of the saddle collar opposite the clamping nut is defined by opposite saddle-shaped edges in one of two orthogonal directions, by bottoms of chamfered corners, and by linear band clamp guiding edges in the other of the two orthogonal directions.

17. The image guided system of claim 16, wherein the linear guiding edges are elevated above the bottoms of the chamfered corners.

18. The image guided system of claim 16, wherein notches are provided in the center of each of the saddle-shaped edges.

19. The image guided system of claim 1, wherein the quick release coupling comprises a cylindrical socket on the mounting head, and a head connector on the mounting assembly, the head connector including a cylindrical plug portion having diametrically projecting lugs engageable in bayonet slots formed in the cylindrical socket.

20. The image guided system of claim 19, wherein the cylindrical socket includes a switch that changes in open/closed state upon insertion and withdrawal of the plug portion into and out of the cylindrical socket.

21. An instrument attachment device for use with a computer controlled surgical navigation system employing a controller in communication with a sensor array for interacting with an instrument mounted position tracking array and tracking positions of an instrument in three dimensional space relative to a known reference point, the instrument attachment device comprising:

a tracking head carrying the position tracking array; and an instrument mounting assembly including a compliant clamping band attachable to the instrument and a head connector enabling adjustment of the relative position between the tracking head and the instrument.

22. A method of computer controlled surgical instrument navigation in which a controller communicates with a sensor array for interacting with an instrument mounted position tracking array on a tracking head and tracks positions of an instrument in three dimensional space relative to a known reference point, the method comprising the steps of:

fixedly mounting an instrument mounting assembly to each of a plurality of surgical instruments to be used in a surgical procedure;

providing for a quick release coupling of the tracking head to the mounting assembly on each of the plurality of surgical instruments; and signalling the controller for each connection and disconnection of the tracking head to each surgical instrument.

23. The method of claim 22 including a step of adjusting the angle of the tracking head to any of the surgical instruments.

* * * * *